(12) United States Patent
Zimmet et al.

(10) Patent No.: US 7,173,012 B2
(45) Date of Patent: Feb. 6, 2007

(54) HYPOGLYCAEMIC PEPTIDES AND METHODS OF USE THEREOF

(75) Inventors: Paul Zev Zimmet, Toorak (AU); Frank Man-Woon Ng, Kew (AU)

(73) Assignees: International Diabetes Institute, Caulfield South (AU); Monash University, Clayton (AU)

( * ) Notice: Subject to any disclaimer, the term of this patent is extended or adjusted under 35 U.S.C. 154(b) by 79 days.

(21) Appl. No.: 10/481,662

(22) PCT Filed: Jun. 27, 2002

(86) PCT No.: PCT/AU02/00840

§ 371 (c)(1),
(2), (4) Date: Aug. 24, 2004

(87) PCT Pub. No.: WO03/002594

PCT Pub. Date: Jan. 9, 2003

(65) Prior Publication Data

US 2005/0032706 A1    Feb. 10, 2005

(30) Foreign Application Priority Data

Jun. 27, 2001    (AU) .................................... PR 5956

(51) Int. Cl.
| | | |
|---|---|---|
| *A61K 38/07* | (2006.01) | |
| *A61K 38/08* | (2006.01) | |
| *C07K 5/103* | (2006.01) | |
| *C07K 7/04* | (2006.01) | |

(52) U.S. Cl. .......................... 514/18; 514/18; 530/326; 530/330

(58) Field of Classification Search ..................... None
See application file for complete search history.

(56) References Cited

U.S. PATENT DOCUMENTS

| | | | | |
|---|---|---|---|---|
| 4,596,790 A | | 6/1986 | Trygstad et al. ............... | 514/18 |
| 5,561,116 A | * | 10/1996 | Nakamura et al. ............ | 514/23 |
| 6,048,840 A | | 4/2000 | Hearn et al. ................... | 514/15 |
| 6,803,189 B2 | * | 10/2004 | Keesee et al. ................. | 435/6 |
| 2004/0198650 A1 | * | 10/2004 | Jensen ........................... | 514/12 |

FOREIGN PATENT DOCUMENTS

WO    WO 98/09170    3/1998

OTHER PUBLICATIONS

Ng et al. Insulin Potentiating Action of a Peptide Fraction from Human Urine. Diabetes. Dec. 1974, vol. 23, No. 12, pp. 950-956.*
Boge, A., et al., "A Nonradioactive Assay for the Insulin Receptor Tyrosine Kinase: Use in Monitoring Receptor Kinase Activity After Activation of Overexpressed Protein Kinase C Alpha and High Glucose Treatment," *Anal. Biochem.* 231(2):323-32, Nov. 1, 1995.

* cited by examiner

*Primary Examiner*—Jeffrey Edwin Russel
(74) *Attorney, Agent, or Firm*—Seed IP Law Group PLLC

(57) ABSTRACT

A peptide of the formula $(Xaa)_{n1}$-$Xaa_1$-His-Thr-Asp-$(Xaa)_{n2}$, wherein Xaa is any amino acid; $Xaa_1$ is a hydrophobic amino acid, preferably Gly or Val; n1 is 0–10; and n2 is 0–10; and use thereof in regulating in vivo blood glucose levels in a human or other mammal, particularly in the treatment of Type 2 diabetes in a human. Preferably, the peptide is a tetrapeptide selected from Gly-His-Thr-Asp and Val-His-Thr-Asp. These hypoglycaemic peptides are isolated from human urine and they also have been chemically synthesized.

9 Claims, 8 Drawing Sheets

In vitro assay of $^{14}C$-glucose conversion into glycogen in the hemi-diaphragm muscles of Zucker rats In vitro assay of $^{14}$C-glucose conversion into
glycogen in the hemi-diaphragm muscles of Zucker rats

SEQUENCE LISTING

<160> NUMBER OF SEQ ID NOS: 11

<210> SEQ ID NO 1
<211> LENGTH: 8
<212> TYPE: PRT
<213> ORGANISM: mammalian

<400> SEQUENCE: 1

Leu Ser Arg Leu Phe Asp Asn Ala
1               5

<210> SEQ ID NO 2
<211> LENGTH: 6
<212> TYPE: PRT
<213> ORGANISM: mammalian
<220> FEATURE:
<221> NAME/KEY: MISC_FEATURE
<222> LOCATION: (1)..(6)
<223> OTHER INFORMATION: Xaa at positions 1 and 6 is (Xaa)n where Xaa is
      any amino acid and n is 0-10;  Xaa at position 2 is a hydrophobic
      amino acid
<220> FEATURE:
<221> NAME/KEY: MISC_FEATURE
<222> LOCATION: (1)..(6)
<223> OTHER INFORMATION: Xaa at positions 1 and 6 is (Xaa)n where Xaa is
      any amino acid and n is 0-10;  Xaa at position 2 is a hydrophobic
      amino acid

<400> SEQUENCE: 2

Xaa Xaa His Thr Asp Xaa
1               5

<210> SEQ ID NO 3
<211> LENGTH: 6
<212> TYPE: PRT
<213> ORGANISM: mammalian
<220> FEATURE:
<221> NAME/KEY: MISC_FEATURE
<222> LOCATION: (1)..(6)
<223> OTHER INFORMATION: Xaa at positions 1 and 6 is (Xaa)n where Xaa is
      any amino acid and n is 0-10.

<400> SEQUENCE: 3

Xaa Gly His Thr Asp Xaa
1               5

<210> SEQ ID NO 4
<211> LENGTH: 6
<212> TYPE: PRT
<213> ORGANISM: mammalian
<220> FEATURE:
<221> NAME/KEY: MISC_FEATURE
<222> LOCATION: (1)..(6)
<223> OTHER INFORMATION: Xaa at positions 1 and 6 is (Xaa)n where Xaa is
      any amino acid and n is 0-10.

<400> SEQUENCE: 4

Xaa Val His Thr Asp Xaa
1               5

<210> SEQ ID NO 5
<211> LENGTH: 4
<212> TYPE: PRT
<213> ORGANISM: mammalian

<400> SEQUENCE: 5

Gly His Thr Asp

```
1

<210> SEQ ID NO 6
<211> LENGTH: 4
<212> TYPE: PRT
<213> ORGANISM: mammalian

<400> SEQUENCE: 6

Val His Thr Asp
1

<210> SEQ ID NO 7
<211> LENGTH: 4
<212> TYPE: PRT
<213> ORGANISM: mammalian

<400> SEQUENCE: 7

Asp His Thr Gly
1

<210> SEQ ID NO 8
<211> LENGTH: 4
<212> TYPE: PRT
<213> ORGANISM: mammalian

<400> SEQUENCE: 8

Val His Thr Pro
1

<210> SEQ ID NO 9
<211> LENGTH: 4
<212> TYPE: PRT
<213> ORGANISM: mammalian
<220> FEATURE:
<221> NAME/KEY: MISC_FEATURE
<222> LOCATION: (1)..(4)
<223> OTHER INFORMATION: Xaa at position 4 is isoAsp.

<400> SEQUENCE: 9

Gly His Thr Xaa
1

<210> SEQ ID NO 10
<211> LENGTH: 4
<212> TYPE: PRT
<213> ORGANISM: mammalian
<220> FEATURE:
<221> NAME/KEY: MISC_FEATURE
<222> LOCATION: (1)..(4)
<223> OTHER INFORMATION: Xaa at position 4 is isoAsp.

<400> SEQUENCE: 10

Val His Thr Xaa
1

<210> SEQ ID NO 11
<211> LENGTH: 4
<212> TYPE: PRT
<213> ORGANISM: mammalian
<220> FEATURE:
<221> NAME/KEY: MISC_FEATURE
<222> LOCATION: (1)..(4)
<223> OTHER INFORMATION: Xaa at position 1 is isoAsp.
```

```
<400> SEQUENCE: 11

Xaa His Thr Gly
1
```

HYPOGLYCAEMIC PEPTIDES AND METHODS OF USE THEREOF

FIELD OF THE INVENTION

The present invention relates generally to a class of hypoglycaemic peptides. More particularly, this invention relates to a method for regulating blood glucose levels of a human or other mammal by administration of a peptide of this class. These hypoglycaemic peptides therefore have potential for use as anti-diabetic agents, particularly in treatment of Type 2 diabetes (or non-insulin-dependent diabetes mellitus, NIDDM).

BACKGROUND OF THE INVENTION

Bibliographic details of the publications referred to hereinafter in this specification are collected at the end of the description.

The reference to any prior art in this specification is not, and should not be taken as, an acknowledgment or any form of suggestion that that prior art forms part of the common general knowledge in Australia.

Type 2 diabetes results in chronic hyperglycaemia, hyperinsulinemia, insulin resistance, impaired insulin secretion and the risk of cardiovascular complications (1–4). A recent report (5) showed that there are more than 150 million people worldwide who suffer from diabetes mellitus, among which over 90% of the people have Type 2 diabetes. Currently, apart from insulin, no molecule of biological origin has been found useful for the treatment and management of Type 2 diabetes without further aggravating hyperinsulinemia which is believed to be a potential cause for the development of diabetes complications.

The isolation of a peptdic factor from human pituitary growth hormone extracts which accelerated glucose uptake in isolated rat hemi-diaphragms has been reported (6,7,8). The structure studies demonstrated that the molecule was a fragment of the amino terminal sequence of the growth hormone molecule. The amino-terminal region of human growth hormone (hGH) containing the amino acid sequence Leu-Ser-Arg-Leu-Phe-Asp-Asn-Ala (hGH 6–13) (SEQ ID NO:1) was found to enhance the actions of insulin in vitro and in vivo (9). This human growth hormone peptide was used for used for comparison in the course of the work on the urinary peptide factors.

Hypoglycaemic action of a semi-purified fraction of human urine has also been observed (10,11). This urinary fraction acted only in the presence of insulin in enhancing glucose uptake, glycogen synthesis, and glycogen synthetase conversion to the active form in vitro and in vivo. The similar in vitro or in vivo biological effects of this urinary fraction led to the assumption that it was the hGH (6–13) fragment of human growth hormone, although no unequivocal evidence was obtained to establish its identity. Studies with ultrafiltration, ion exchange and gel filtration chromatography indicated that the isolate from human urine was a peptidic compound (11).

In work leading to the present invention, the hypoglycaemic peptide in human urine has been isolated and purified, and its structure determined. In addition, this peptide has been chemically synthesised. The activity of both the isolated peptide and the chemically synthesised peptide have been examined in vitro and in vivo to demonstrate its insulin-potentiating effects by enhanced glucose uptake and glycogen synthesis in vitro and lowered blood glucose levels in vivo. In addition, peptide analogues of this isolated peptide have also been chemically synthesised, and certain of these analogues have also been shown to have significant biological effects on glucose metabolism both in vitro and in vivo.

SUMMARY OF THE INVENTION

In one aspect, the present invention provides a peptide of the formula:

$$(Xaa)_{n1}\text{-}Xaa_1\text{-}His\text{-}Thr\text{-}Asp\text{-}(Xaa)_{n2} \quad (\text{SEQ ID NO:2})$$

wherein
Xaa is any amino acid;
$Xaa_1$ is a hydrophobic amino acid;
$n_1$ is 0–10; and
$n_2$ is 0–10.

In a preferred embodiment of this aspect of the invention, the present invention provides a peptide of the formula:

$$(Xaa)_{n1}\text{-}Gly\text{-}His\text{-}Thr\text{-}Asp\text{-}(Xaa)_{n2} \quad (\text{SEQ ID NO:3})$$

or $$(Xaa)_{n1}\text{-}Val\text{-}His\text{-}Thr\text{-}Asp\text{-}(Xaa)_{n2} \quad (\text{SEQ ID NO:4})$$

wherein Xaa, $n_1$ and $n_2$ are as defined above.

Preferably, the peptide is a tetrapeptide selected from:
Gly-His-Thr-Asp (hereinafter identified as UP-401) (SEQ ID NO:5); and
Val-His-Thr-Asp (hereinafter identified as UP-402) (SEQ ID NO:6).

In another aspect, the present invention provides the isolated tetrapeptide Gly-His-Thr-Asp (SEQ ID NO:5), in substantially purified form.

In a further aspect, the present invention provides a method of regulating in vivo blood glucose levels in a human or other mammal, which comprises administration to said human or other mammal of an effective amount of a peptide of the formula:

$$(Xaa)_{n1}\text{-}Xaa_1\text{-}His\text{-}Thr\text{-}Asp\text{-}(Xaa)_{n2} \quad (\text{SEQ ID NO:2})$$

wherein
Xaa is any amino acid;
$Xaa_1$ is a hydrophobic amino acid;
$n_1$ is 0–10; and
$n_2$ is 0–10.

In preferred embodiments of this aspect of the invention, the peptide is a peptide of the formula:

$$(Xaa)_{n1}\text{-}Gly\text{-}His\text{-}Thr\text{-}Asp\text{-}(Xaa)_{n2} \quad (\text{SEQ ID NO:3})$$

or $$(Xaa)_{n1}\text{-}Val\text{-}His\text{-}Thr\text{-}Asp\text{-}(Xaa)_{n2} \quad (\text{SEQ ID NO:4})$$

wherein Xaa, $n_1$ and $n_2$ are as defined above.

Preferably, in this aspect of the invention, the peptide is a tetrapeptide selected from:
Gly-His-Thr-Asp (UP-401) (SEQ ID NO:5); and
Val-His-Thr-Asp (UP-402) (SEQ ID NO:6).

In yet another aspect, the present invention provides use of a peptide of the formula:

$$(Xaa)_{n1}\text{-}Xaa_1\text{-}His\text{-}Thr\text{-}Asp\text{-}(Xaa)_{n2} \quad (\text{SEQ ID NO:2})$$

wherein
Xaa is any amino acid;
$Xaa_1$ is a hydrophobic amino acid;
$n_1$ is 0–10; and
$n_2$ is 0–10, in the manufacture of a composition for regulating in vivo blood glucose levels in a human or other mammal.

In preferred embodiments of this aspect of the invention, the peptide is a peptide of the formula:

$(Xaa)_{n1}$-Gly-His-Thr-Asp-$(Xaa)_{n2}$ (SEQ ID NO:3)

or $(Xaa)_{n1}$-Val-His-Thr-Asp-$(Xaa)_{n2}$ (SEQ ID NO:4)

wherein Xaa, $n_1$ and $n_2$ are as defined above.

Preferably, in this aspect of the invention, the peptide is a tetrapeptide selected from:

Gly-His-Thr-Asp (UP-401) (SEQ ID NO:5); and
Val-His-Thr-Asp (UP-402) (SEQ ID NO:6).

The present invention also provides a pharmaceutical composition for regulating in vivo blood glucose levels in a human or other mammal, which comprises the peptide of the formula:

$(Xaa)_{n1}$-$Xaa_1$-His-Thr-Asp-$(Xaa)_{n2}$ (SEQ ID NO:2)

wherein
Xaa is any amino acid;
$Xaa_1$ is a hydrophobic amino acid;
$n_1$ is 0–10; and
$n_2$ is 0–10, together with one or more pharmaceutically acceptable carriers and/or diluents.

In preferred embodiments of this aspect of the invention, the peptide is a peptide of the formula:

$(Xaa)_{n1}$-Gly-His-Thr-Asp-$(Xaa)_{n2}$ (SEQ ID NO:3)

or $(Xaa)_{n1}$-Val-His-Thr-Asp-$(Xaa)_{n2}$ (SEQ ID NO:4)

wherein Xaa, $n_1$ and $n_2$ are as defined above.

Preferably, in this aspect of the invention, the peptide is a tetrapeptide selected from:

Gly-His-Thr-Asp (UP-401) (SEQ ID NO:5); and
Val-His-Thr-Asp (UP-402) (SEQ ID NO:6).

Preferably, in the peptides of this invention the amino acids are in the L-form, however the present invention also extends to peptides in which one or more of the amino acids are in the D-, α- or β-form.

Throughout this specification, unless the context requires otherwise, the word "comprise", and or variations such as "comprises" or "comprising", will be understood to imply the inclusion of a stated integer or step or group of integers or steps but not the exclusion of any other integer or step or group of integers or steps.

DETAILED DESCRIPTION OF THE INVENTION

The present invention relates to a class of hypoglycaemic peptides which may be used to regulate in vivo blood glucose levels in a human or other mammal. Regulation of blood glucose levels, particularly lowering of these levels, provides a method for treatment of diabetes in humans, particularly treatment of Type 2 diabetes.

The peptides of the invention have the formula:

$(Xaa)_{n1}$-$Xaa_1$-His-Thr-Asp-$(Xaa)_{n2}$ (SEQ ID NO:2)

wherein
Xaa is any amino acid;
$Xaa_1$ is a hydrophobic amino acid;
$n_1$ is 0–10; and
$n_2$ is 0–10.

Preferably, the hydrophobic amino acid is selected from the group consisting of Gly, Ala, Leu, Ile, Phe or Val. Most preferably, the hydrophobic amino acid is Gly or Val.

Particularly preferred peptides of the invention are:
Gly-His-Thr-Asp (UP-401) (SEQ ID NO:5); and
Val-His-Thr-Asp (UP-402) (SEQ ID NO:6).

Preparation

The peptides of the invention as described above may be synthesised using conventional liquid or solid phase synthesis techniques. For example, reference may be made to solution synthesis or solid phase synthesis as described in Chapter 9, entitled "Peptide Synthesis" by Atherton and Shephard, which is included in the publication entitled "*Synthetic Vaccines*" edited by Nicholson and published by Blackwell Scientific Publications. Preferably, a solid phase peptide synthesis technique using Fmoc chemistry is used, such as the Merrifield synthesis method (12,13).

Alternatively, these peptides may be prepared as recombinant peptides using standard recombinant DNA techniques. Thus, a recombinant expression vector containing a nucleic acid sequence encoding the peptide and one or more regulatory sequences operatively linked to the nucleic acid sequence to be expressed may be introduced into and expressed in a suitable prokaryotic or eukaryotic host cell, as described, for example, in Gene Expression Technology: Methods in Enzymology, 185, Academic Press, San Diego, Calif. (1990), and Sambrook et al., Molecular Cloning: A Laboratory Manual, $2^{nd}$ ed. Cold Spring Harbor Laboratory Press, Cold Spring Harbor, N.Y. (1989).

The UP-401 peptide may also be isolated from human urine by standard protein purification procedures, preferably using reversed-phase high performance liquid chromatography (RP-HPLC). Using these procedures, UP-401 is obtained in isolated form. By "isolated" is meant a peptide material that is substantially or essentially freed from components, particularly other proteins and peptides, that normally accompany it in its native state in human urine by at least one purification or other processing step.

Such isolated UP-401 may also be described as substantially pure. The term "substantially pure" as used herein describes peptide material that has been separated from components that naturally accompany it. Typically, peptide material is substantially pure when at least 70%, more preferably at least 80%, even more preferably at least 90%, and most preferably at least 95% or even 99% of the total material (by volume, by wet or dry weight, or by mole percent or mole fraction) is the peptide of interest. Purity can be measured by any appropriate method, for example, in the case of peptide material, by chromatography, gel electrophoresis or HPLC analysis.

Formulations

The present invention also extends to pharmaceutical compositions for regulating in vivo blood glucose levels in humans or other mammals which comprise a peptide of the invention as described above, together with one or more pharmaceutically acceptable carriers and/or diluents.

The formulation of such therapeutic compositions is well known to persons skilled in this field. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically active substances is well known in the art, and it is described, by way of example, in *Remington's Pharmaceutical Sciences*, 18th Edition, Mack Publishing Company, Pennsylvania, USA. Except insofar as any conventional media or agent is incompatible with the active ingredient, use thereof in the pharmaceutical compositions of the present invention is contemplated. Supplementary active ingredients can also be incorporated into the compositions.

It is especially advantageous to formulate such compositions in dosage unit form for ease of administration and uniformity of dosage. Dosage unit form as used herein refers to physically discrete units suited as unitary dosages for the human or other mammalian subjects to be treated; each unit contains a predetermined quantity of active ingredient calculated to produce the desired therapeutic effect in association with the required pharmaceutical carrier and/or diluent. The specifications for the novel dosage unit forms of the invention are dictated by and directly dependent on (a) the unique characteristics of the active ingredient and the particular therapeutic effect to be achieved, and (b) the limitations inherent in the art of compounding such an active ingredient for the particular treatment.

Administration

The present invention further extends to the methods for regulating in vivo blood glucose levels in humans or other mammals by administering an effective amount of a peptide of the invention as described above. Preferably, this treatment is administered to a human or other mammal in need of therapeutic or prophylactic treatment for a disease condition or potential disease condition. Most preferably, the treatment is treatment of Type 2 diabetes in a human.

A variety of administration routes are available. The particular mode selected will depend, of course, upon the particular condition being treated and the dosage required for therapeutic efficacy. The methods of this invention, generally speaking, may be practised using any mode of administration that is medically acceptable, meaning any mode that produces therapeutic levels of the active component of the invention without causing clinically unacceptable adverse effects. Such modes of administration include parenteral (e.g. subcutaneous, intramuscular and intravenous), oral, rectal, topical, nasal and transdermal routes.

The active component may conveniently be presented in unit dosage form and suitable compositions for administration may be prepared by any of the methods well known in the art of pharmacy. Such methods include the step of bringing the active component into association with a carrier and/or diluent which may include one or more accessory ingredients. In general, the compositions are prepared by uniformly and intimately bringing the active component into association with a liquid carrier, a finely divided solid carrier, or both, and then, if necessary, shaping the product.

Compositions suitable for parenteral administration conveniently comprise a sterile aqueous preparation of the active component which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in polyethylene glycol and lactic acid. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono-or di-glycerides. In addition, fatty acids such as oleic acid find use in the preparation of injectables.

Compositions of the present invention suitable for oral administration may be presented as discrete units such as capsules, cachets, tablets or lozenges, each containing a predetermined amount of the active component, in liposomes or as a suspension in an aqueous liquor or non-aqueous liquid such as a syrup, an elixir, or an emulsion.

Other delivery systems can include sustained release delivery systems. Preferred sustained release delivery systems are those which can provide for release of the active component of the invention in sustained release pellets or capsules. Many types of sustained release delivery systems are available; these include, but are not limited to: (a) erosional systems in which the active component is contained within a matrix, and (b) diffusional systems in which the active component permeates at a controlled rate through a polymer.

The active component is administered in therapeutically effective amounts. A therapeutically effective amount means that amount necessary at least partly to attain the desired effect, or to delay the onset of, inhibit the progression of, or halt altogether, the onset or progression of the particular condition being treated. Such amounts will depend, of course, on the particular condition being treated, the severity of the condition and individual patient parameters including age, physical condition, size, weight and concurrent treatment. These factors are well known to those of ordinary skill in the art and can be addressed with no more than routine experimentation. It is preferred generally that a maximum dose be used, that is, the highest safe dose according to sound medical judgement. It will be understood by those of ordinary skill in the art, however, that a lower dose or tolerable dose may be administered for medical reasons, psychological reasons or for virtually any other reasons.

Generally, daily oral doses of active component will be from about 0.01 mg/kg per day to 1000 mg/kg per day. Small doses (0.01–1 mg) may be administered initially, followed by increasing doses up to about 1000 mg/kg per day. In the event that the response in a subject is insufficient at such doses, even higher doses (or effective higher doses by a different, more localised delivery route) may be employed to the extent patient tolerance permits. Multiple doses per day are contemplated to achieve appropriate systemic levels of compounds.

Further features of the present invention are more fully described in the following Example(s). It is to be understood, however, that this detailed description is included solely for the purposes of exemplifying the present invention, and should not be understood in any way as a restriction on the broad description of the invention as set out above.

BRIEF DESCRIPTIONS OF THE DRAWINGS

Figure 4:
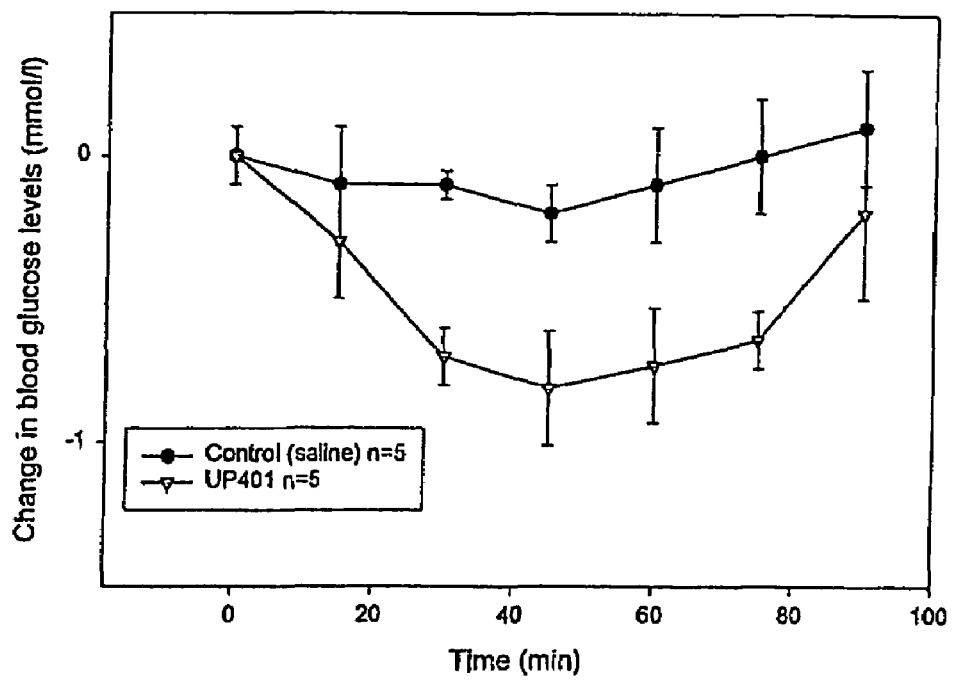

FIG. 4 shows the in vivo effect of UP-401 peptide on glycogen metabolism. Data represent the mean +/− SEM of five independent experiments. The changes in blood glucose levels were statistically significant (p<0.005) as compared with control.

Figure 5:
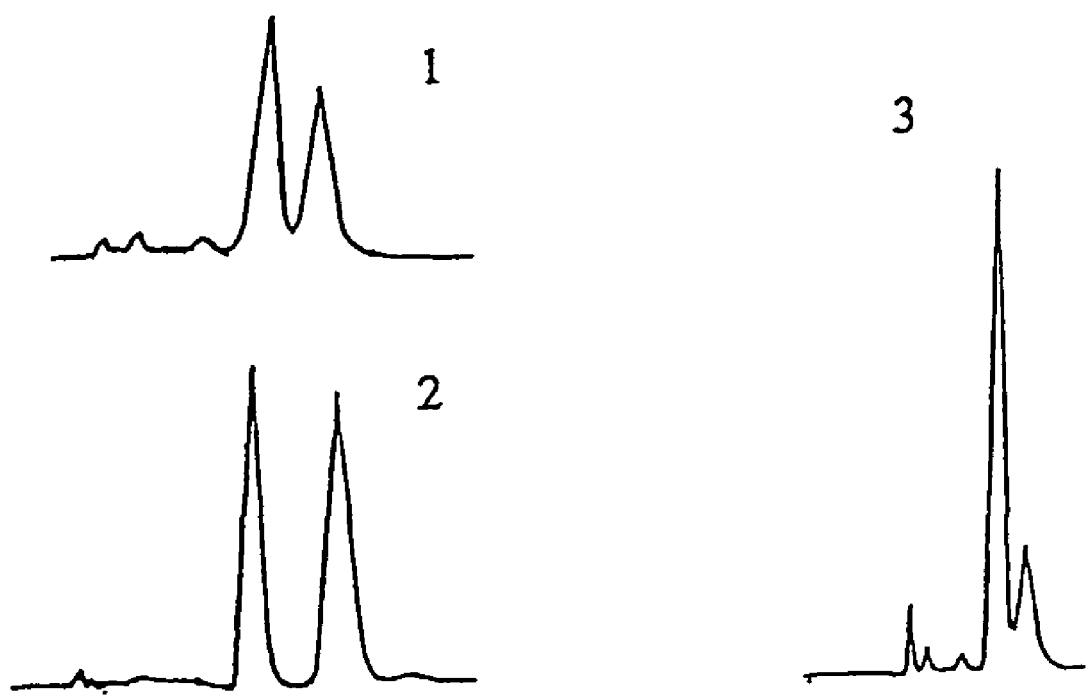

FIG. 5 shows the HPLC profiles of peptides 1, 2 and 3 (see Table 2). A mixture of synthetic peptides (Gly-His-Thr-Asp, Val-His-Thr-Asp and Asp-His-Thr-Gly) and their corresponding β-isomerised formation (Gly-His-Thr-βAsp, Val-His-Thr-βAsp and βAsp-His-Thr-Gly) were separated by reverse-phase HPLC and eluted with an isocritic running with 2% buffer B (buffer A is 0.1% trifluoroacetic acid in $H_2O$) at 1 ml/min over 30 min. Peptides were determined by their absorbance at 214 nm.

Figure 6:
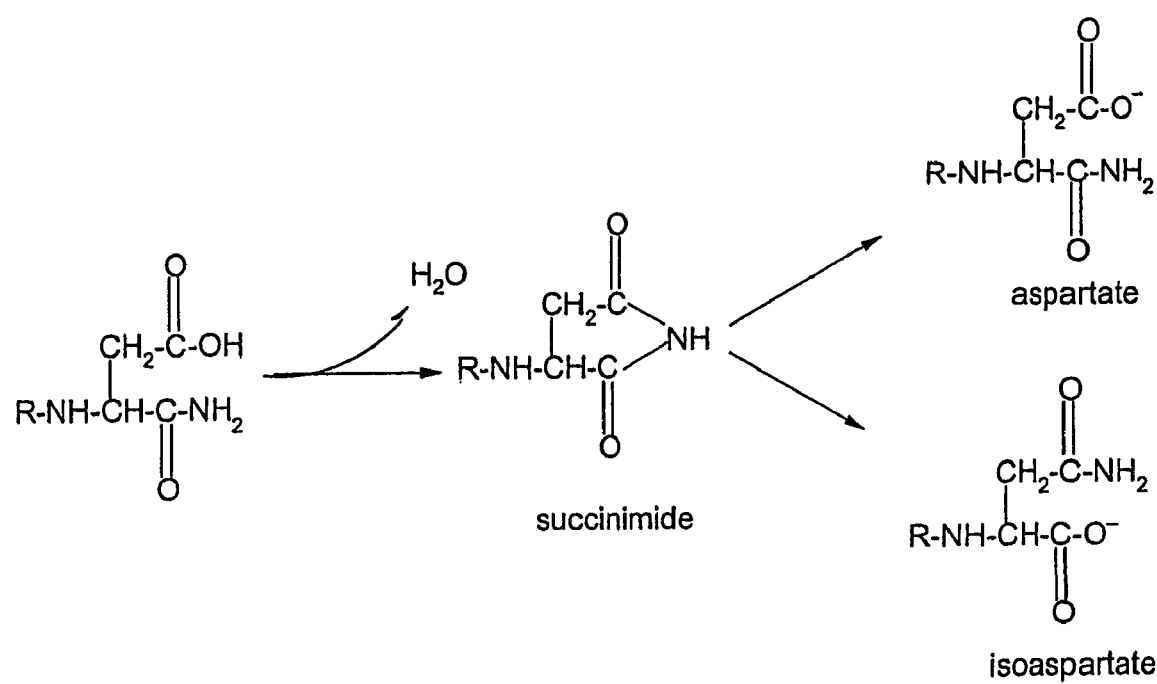

FIG. 6 shows β-isomerisation of the N-terminal Asp-X sequence. Attack by the peptide backbone nitrogen of the carbonyl group can result in the formation of a five membered succinimide ring. The succinimide ring is prone to hydrolysis, producing ring nonisomerised (Asp) and β-isomerised (βAsp) peptides in a ratio of ca. 1:3 when the site is Asp-His.

Figure 7:
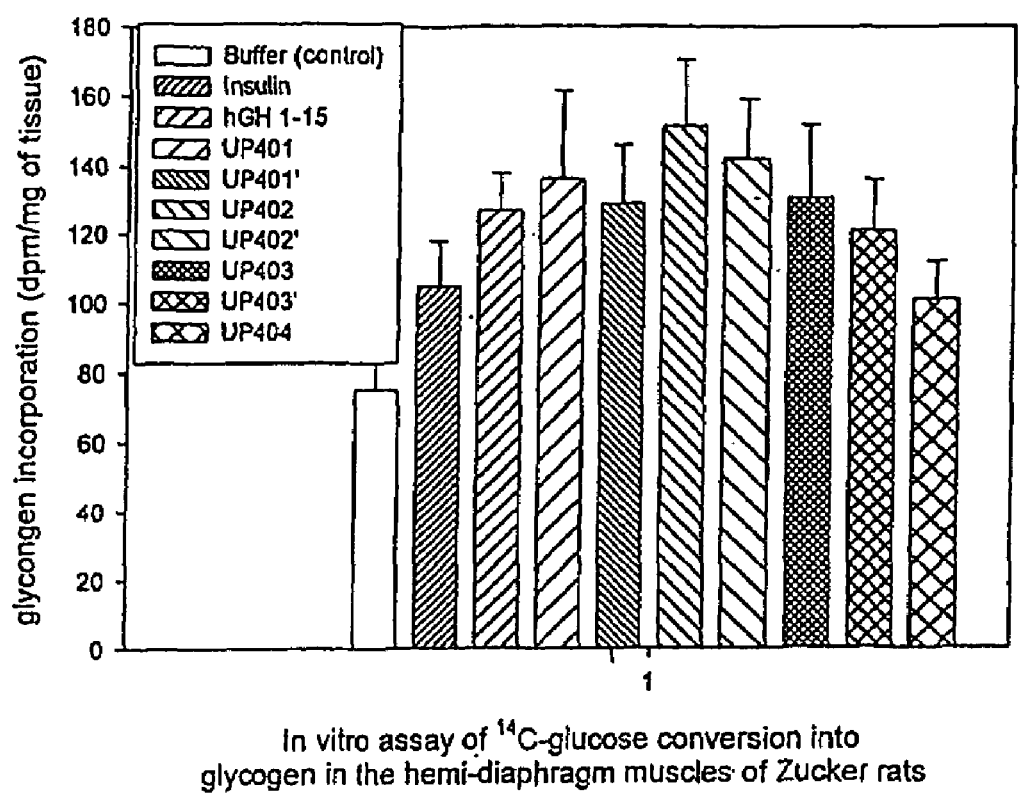

FIG. 7 shows stimulation of glycogen synthase activity in tissue by insulin and by synthetic peptides UP-401, UP-401[1], UP-402, UP-402[1], UP-403, UP-403[1], UP-404 and hGH1–15.

Figure 8:
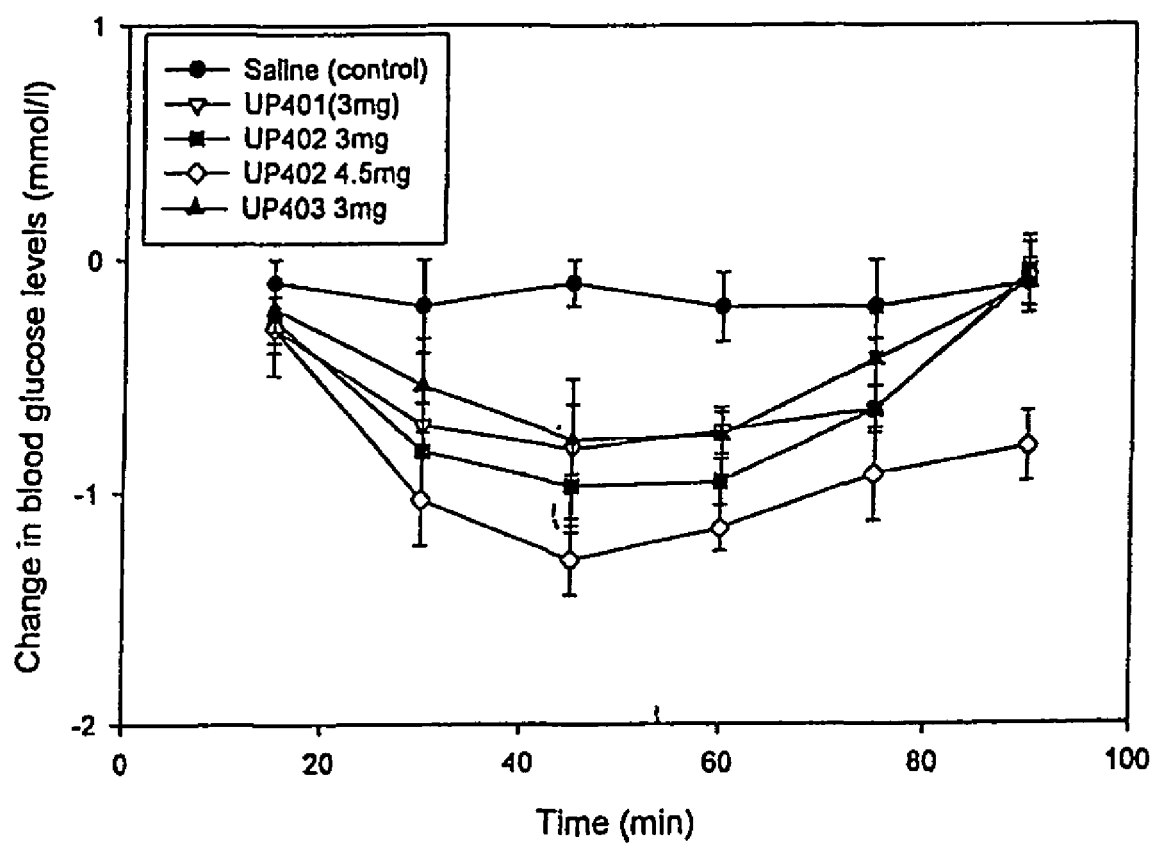

FIG. 8 shows the in vivo effect of UP-401 peptide and analogues UP-402 and UP-403 on glycogen metabolism. Data represent the mean +/− SEM of five independent experiments. The changes in blood glucose levels were statistically significant (p<0.005) as compared with control.

EXAMPLE 1

In this Example, we have isolated and characterised the UP-401 peptide from human urine, chemically synthesised UP-401 and examined its activity in vitro and in vivo. Results suggest that UP-401 exhibits insulin-potentiating effects, as demonstrated by the enhanced glucose uptake and glycogen synthesis in vitro and lowered blood glucose level in vivo.

Materials and Methods

Materials

All chemicals and reagents used for peptide synthesis were purchased from Auspep Pty.Ltd. (Melbourne, Australia), except for ninhydrin test kit from PerElmer. Acetonitrile was purchased from Mallinckrodt Specialty Chemicals (Melbourne, Australia). 1,3-Diisopropylcarbodiimide was from Aldrich Chemical Company (Milliford, Mass. U.S.A.). Insulin (100 U/ml) and bovine serum albumin (BSA) were obtained from the Commonwealth Serum Laboratories (Melbourne, Australia), D-glucose (A.R.) from BDH Chemicals Australia Pty. Ltd. (Kilsyth) and D-$^{14}$C(U)glucose from NEN (Boston, USA).

Purification of Human Urinary Material

Urine specimens were collected from normal subjects and processed as described by Ng, et al, (11). In brief, urine was acidified with HCl to pH 2.1 and concentrated using the Diaflo ultrafiltration technique. The crude samples were chromatographed first on Dowex 50W-X2 and then on Amberlite CG50 columns. The fractions containing the biologically active material were eluted from the CG50 column with $H_2O$ and lyophilised.

The crude urinary peptide material was further purified in a number of consecutive reverse-phase HPLC steps as described below.

The lyophilised semi-purified urinary material was dissolved in 0.1% trifluoroacetic acid (TFA) (v/v) and eluted with isocratic elution of 0.1% TFA for 5 min and then a linear gradient of 50% acetonitrile using a Vydec C18 column (4.6×250 mm). Seven fractions were collected, freeze-dried, redissolved in saline (0.9% NaCl) and assayed for biological activity in vitro, using $^{14}$C-glucose incorporation into $^{14}$C-glycogen in rat hemi-diaphragm muscle as an index.

Fraction 1 containing most of the biological activity was dissolved in 0.1% trifluoroacetic acid and further purified using a Vydac C3 column (4.6×250 mm). The sample was eluted with an isocratic condition with a mixture of solvents at a flow rate of 0.1 ml/min. The elutant was made up with solvent A (0.1% TFA in $H_2O$) and solvent B (0.1% TFA in 50% acetonitrile). Three fractions were collected, freeze-dried, redissolved in saline (0.9% NaCl) and assayed in vitro for biological activity as before. The first fraction again contained the most active material and was subjected to re-purification on HPLC using a Vydac C3 column as previously described. This repeat HPLC run yielded the active pure material in Fraction 3 which was then lyophilised for structure studies.

HPLC Equipment

RP-HPLC was performed on a Waters 600 E multisolvent delivery system (Eschbom, Germany) with a scanning Model 484 Tunable Absorbance detector (Millipore, USA) and an extended wavelength module equipped with a 214 nm cut-off filter. The peptides were purified on a 3 µm Vydac C18 (4.6×250 mm) and C3 (4.6×250 mm) columns. The effluents were monitored for peptide bonds by UV absorption at 214 nm at room temperature.

Peptide Sequence Analysis

N-terminal sequencing of the selected peptide fraction was performed using an ASI 477 'pulse liquid' protein sequencer with an on-line ABI 120 A analyser (Applied Biosystems, Inc. Model 475 A).

Mass Spectrometry Analysis

The urinary peptide and the synthetic analogues at a concentration of about 1.0 mM were dissolved in an acetonitrile/water mixture (v/v). A 10 µl sample was injected with a loop injector into a carried stream of acetonitrile/water (50/50) pumped at 10 µl/min into the electrospray ion-source. Mass spectra were performed on a Fisons Instrument, Model VG Platform II (Micromass Ltd., Cheshire, UK) micromass platform instrument. The single charged pseudo-molecular ions (M+H)$^+$ were selected for collision-induced dissociation in the second quadruple and for mass analysis of the daughter ions formed. The mass spectrometry experiments were performed with electrospray with positive ion polarity and the cone voltage=70V @400 m/z to 30V @1200 m/z.

Peptide Synthesis

Peptide syntheses were performed by standard solid-phase peptide synthesis method using Fmoc as the N-amino protecting group (12,14). Couplings were carried out using the DIC+HOBt method (15).

Animals

Male Wistar rats of 380–450 g (10 week) and male Zucker (fa/fa) fatty rats of 400–500 g (10 week) were used for the studies. The animals were housed in the Departmental animal house under the conditions of constant temperature with a 12 h light, 12 h dark cycle and fed ad libitum. The animals used in this investigation were cared for by trained animal technicians in the Monash University Department of Biochemistry and Molecular Biology. All experiments were approved by the Standing Committee on Ethics in Animal Experimentation of Monash University.

In Vivo Biological Assay

In vivo tests of the hypoglycaemic peptides were performed on overnight-fasted male Zucker fatty (fa/fa) rats 45 min after induction of anaesthesia with an intraperitoneal injection of sodium pentobarbitone at a dose 60 mg/kg body weight. Basal blood glucose samples were collected from the cut tip of the tail. The two femoral veins in the anaesthetised animals were then exposed, followed immediately by an intravenous injection of saline (control) or peptide into the left femoral vein. Approximately 15 min after the administration of peptide or saline via the left femoral vein, insulin was injected via the right femoral vein. Blood samples were taken at 5, 10, 15, 30, 45, 60 and 90 min after injection of insulin. Blood glucose levels of the collected samples were measured immediately by the glucose oxidation method using a Yellow Springs YSI modal 2300 STAT Glucose Analyzer (Yellow Spring, Ohio).

In Vitro Biological Assay

Glycogen synthesis in isolated rat hemidiaphragm muscle was measured by the rate of incorporation of radioactive glucose into glycogen (16). Overnight-fasted male albino Wistar rats (20 week old) were killed by decapitation and their hemidiaphragm tissues immediately removed. The hemidiaphragm tissues were pre-incubated for 30 min at 37° C., in Kreb's-Ringer bicarbonate buffer (KRB) containing 1.0% bovine serum albumin BSA, and 1.0 mg/ml glucose gassed pH 7.4. After pre-incubation, the tissues were further incubated for 60 min at 37° C. in 2 ml of incubation buffer in the presence of insulin at a concentration 0.33 µu/ml and the label $^{14}$C-glucose at 0.28 µCi/ml under an atmosphere of carbogen with or without peptide of various concentrations. At the end of the incubation, the tissues were removed and rinsed with cold distilled water, blotted and placed in a plastic centrifuge tubes for glycogen extraction with 30% KOH 10 µl/mg tissue for 5 min in a boiling water bath. The tissue $^{14}$C-glycogen was precipitated with saturated $Na_2SO_4$ and absolute alcohol. After centrifugation at 4000×G at 4° C. for 10 min, the supematant was discarded and the precipitate washed twice by resuspending in 66% ethanol and centrifuged as before. The final glycogen precipitate was dissolved in distilled water 30 µl/mg and 1.0 ml of the solution was transferred to a counting vial containing a triton scintillator (8 ml). Radioactivity was determined in a Wallac LKB counter from Pharmacia-Wallac Oy, (Turku, Finland). The total glycogen content in the diaphragm muscle was calculated according to the method of Van Handel (17).

Results

Figure 1:
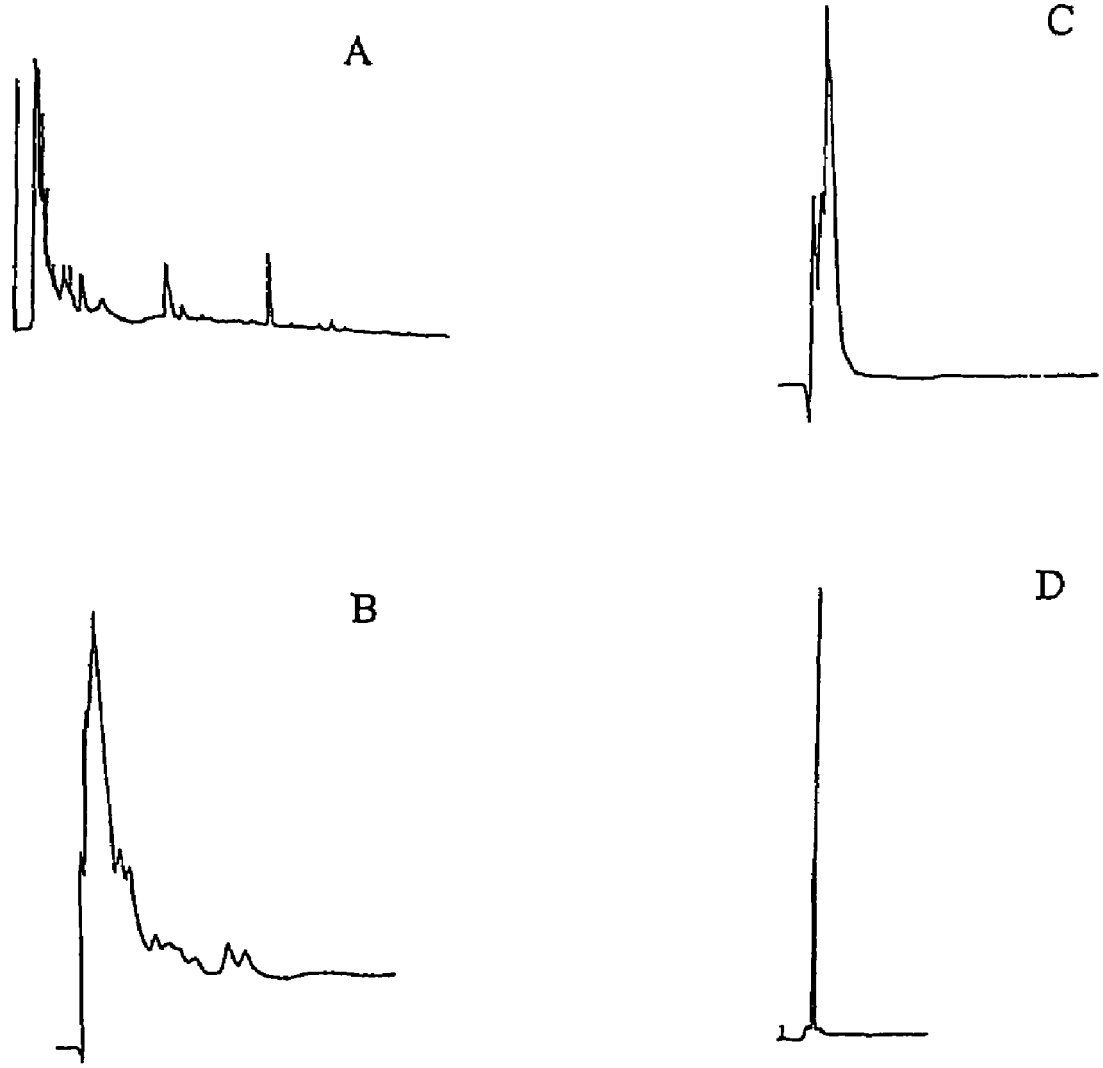
FIG. 1 shows separation of a semi-purified urinary peptide on C18(A) and C3 (B, C and D) columns by four-step reversed-phase HPLC procedures.

The highly purified peptide was obtained from human urine specimens with multiple runs in reverse-phase HPLC. The bioassay of separated fractions was determined at each step. In the first HPLC run, trifluoroacetic acid was used as an ion-pairing agent. The urine specimens consisted of a variety of different hydrophilic and hydrophobic molecules as shown by the elution profiles in FIG. 1A. Seven fractions were collected and assayed in vitro using glycogen synthesis in rat hemidiaphragm muscle as an index of bioactivity. Fraction 1 exhibited higher biological activity on glycogen synthesis than that of all other fractions and was selected for further purification. FIG. 1B shows the reverse-phase elution profile of the fraction in which five fractions were collected for assays in vitro.

The third fraction with the highest bioactivity was lyophilised and subjected to further HPLC purification. The reverse-phase elution profile of the third fraction from B revealed several different peaks (FIG. 1C). Four fractions were also collected and assayed in vitro in which fraction 3, showing higher activity on glycogen synthesis than that of all other fractions, was lyophilised and subjected to a final purification for structure analysis. The purity of the urinary peptide was assessed with amino acid sequence analysis and mass spectrometry.

Amino Acid Sequence Analysis of Purified Urinary Peptide

The N-terminal amino acid sequence analysis of the final pure urinary peptide revealed that the primary structure is Gly-His-Thr-Asp. This peptide is hereinafter referred to as the UP-401 peptide.

Determination of Mass Spectrometry

Figure 2:
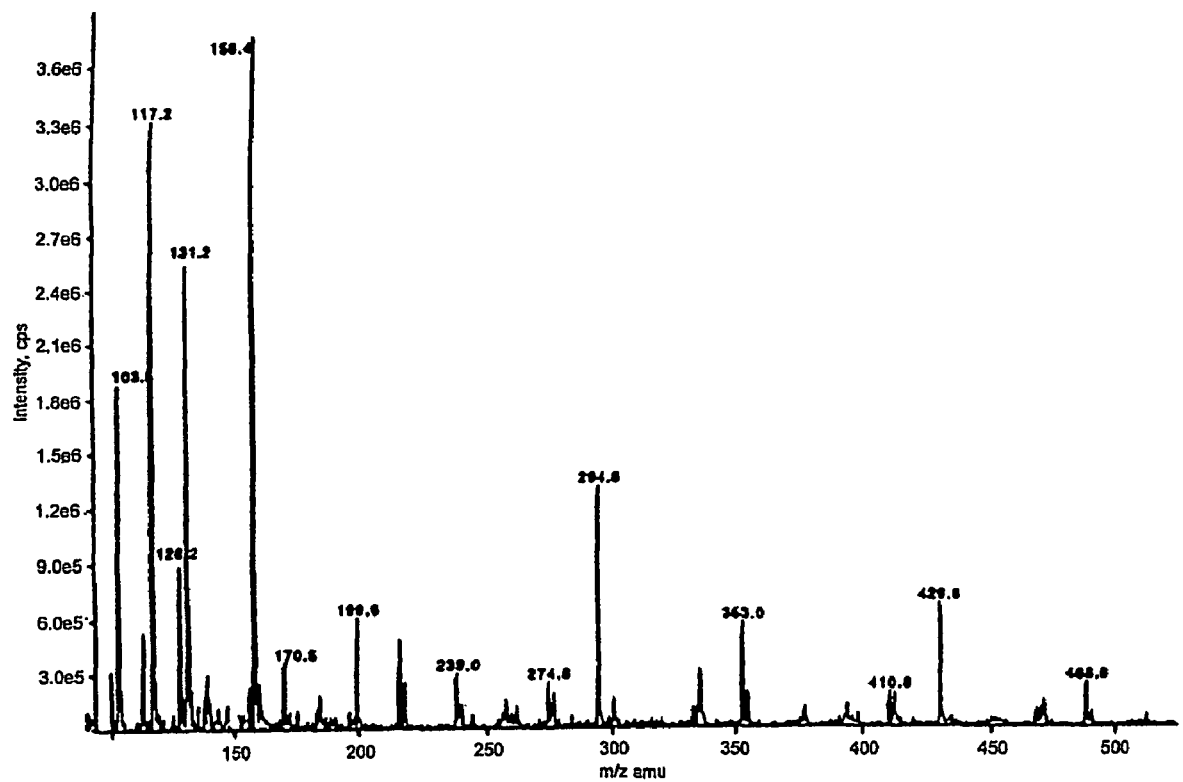
FIG. 2 shows the mass spectrum of the urinary peptide UP-401.

The purity of the UP-401 peptide obtained by HPLC was assessed with mass spectrometry. The UP-401 peptide in the positive ion mode revealed a single predominant ion corresponding to the protonated molecule (M+H$^+$) at m/z 429.8 with few impurities (FIG. 2). This molecular mass was 428 Da from the final purification with HPLC (FIG. 1D) and exclusively responsible for the size of sequenced fragment from amino acid sequence analysis. Reduction of protonated molecule (M+H$^+$) to dehydrated molecule resulted in a net decrease of 18 Da due to the loss of a hydrogen molecule. Reduction of molecule weight 410 Da (Asp-His-Thr-Gly) to 353 Da (His-Thr-Gly) resulted in a net decrease of 57 Da due to the loss of an Asp residue. The molecule weight with m/z 429.8 Da was reduced to m/z 274 Da due to the loss of a histidine as well as an Asp residue.

Based on the revealed structure of the UP-401 peptide, a synthetic peptide corresponding to its sequence was made. The synthetic UP-401 peptide was purified by RP-HPLC using a C18 column and confirmed by mass spectrometry.

Biological Activity of Urinary Peptide Analogues

Figure 3:
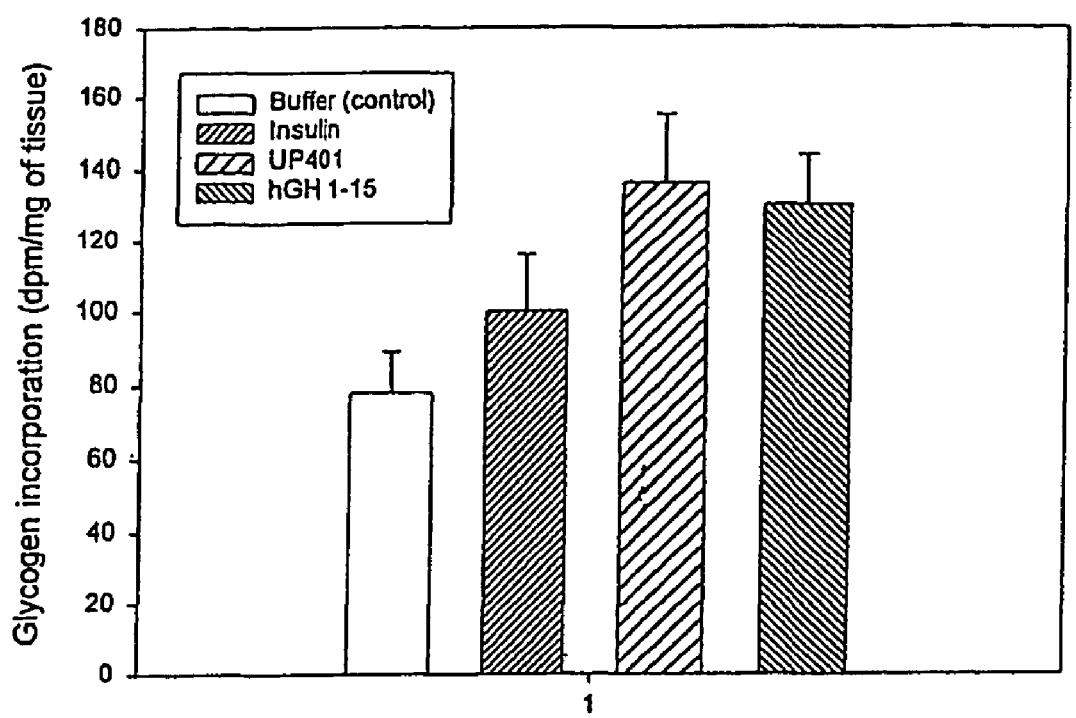
FIG. 3 shows stimulation of glycogen synthase activity in isolated rat hemi-diaphragm muscle tissue by insulin and by synthetic peptides UP-401 and hGH (1–15) (0.1 µM).

The biological action of the UP-401 peptide was examined and results are shown on FIG. 3. A 36.3% increase of glycogen synthesis by UP-401 was determined, which showed a better insulin-potentiating effect than that of the known insulin-potentiating hGH(6–13) peptide. Furthermore, the in vivo effect on blood glucose level was observed after administration of the UP-401 peptide at a dose of 3 mg/kg body weight (FIG. 4). The in vivo hypoglycaemic action of UP-401 in the male Zucker fatty (fa/fa) rats was found 15 minutes after the injection, with maximal effect 45 minutes after treatment, and diminished after 90 minutes. The hypoglycaemic effect of UP-401 was found significant when compared to the control animals treated with saline.

Discussion

Although a crude fraction from human urine has been shown (10,11) to have similar biological activity in vitro and in vivo to the synthetic peptides containing the human growth hormone sequence 1–15 (hGH 1–15), no evidence was provided to indicate the molecular structure of the active component. In this Example, techniques, such as HPLC, amino acid sequencing, and mass spectroscopy, have been used for the purification and characterization of the structure of active compound, UP-401. All data suggest that the UP-401 is a tetrapeptide with the primary structure Gly-His-Thr-Asp. The scientific evidence was further confirmed by making synthetic UP-401 and testing its biological activities. Results from the in vitro metabolic action on glycogen synthesis as well as the in vivo animal trials on lowering blood glucose both demonstrated the insulin potentiating-effect of the UP-401 peptide.

EXAMPLE 2

This study focuses on improving the biological potency of the UP-401 peptide by studying the structure-actvity relationship. Peptide analogues were designed and made by either replacing or isomerising the residues of UP-401 and biological assays were conducted to test the potency of each designed analogue.

Materials and Methods

Materials

See Example I.

Peptide Synthesis

Syntheses of peptide analogues were performed by a standard solid-phase peptide synthesis method using Fmoc Chemistry (12). As in Example 1, couplings for peptide bond formation were carried out using the DIC+HOBt method (15) and purification was also conducted by reverse-phase HPLC methodology.

Mass Spectrometry Analysis

The molecular structure of each peptide analogue was confirmed by determining its molecular weight, using the electrospray mass spectrophotometer as described in Example 1.

In vitro and in vivo Biological Assays

Experimental procedures for the in vitro and in vivo assays were described in Example 1. In principle, the rate of conversion from glucose into glycogen in isolated hemidiaphragm muscle was used as the index to determine the in vitro activity of peptides (6). The in vivo tests for the peptides were performed on Zucker fatty (fa/fa) rats by i.v. administration of peptides and the reduction of the blood glucose levels was measured and regarded as the index of the hypoglycaemic effect (18).

Results

Based on the structure of the UP-401 peptide, analogues with various sequences were synthesised for further biological characterization as shown in Table 1. All synthetic peptides were purified by RP-HPLC using a C18 column and characterized by mass spectrometry. During synthesis, the peptide chains were treated with base (piperidine) in deprotection steps and then eventually treated with TFA at cleavage steps.

TABLE 1

The primary sequence of urinary peptide and the synthetic analogues

| Peptide Analogues | Sequence |
| --- | --- |
| UP-401 | Gly-His-Thr-Asp-NH$_2$ |
| UP-402 | Val-His-Thr-Asp-NH$_2$ |
| UP-403 | Asp-His-Thr-Gly-NH$_2$ |
| UP-404 | Val-His-Thr-Pro-NH$_2$ |
| UP-405 | Gly-His-Thr-isoAsp-NH$_2$ |

TABLE 1-continued

The primary sequence of urinary peptide and the synthetic analogues

| Peptide Analogues | Sequence |
| --- | --- |
| UP-406 | Val-His-Thr-isoAsp-NH$_2$ |
| UP-407 | isoAsp-His-Thr-Gly-NH$_2$ |

Table 2 and FIG. 5 outline the amino acid sequence of the UP-401 peptide and its analogues, and the ratio of nonisomerized and β-isomerised peptide obtained in each.

TABLE 2

The primary sequence of urinary peptide and the structures of urinary peptide analogues.

| Peptide No. | Sequence | Isoasp |
| --- | --- | --- |
| 1 | Gly-His-Thr-Asp-NH$_2$ | 45.2 |
| 2 | Val-His-Thr-Asp-NH$_2$ | 48.3 |
| 3 | Asp-His-Thr-Gly-NH$_2$ | 75.2 |
| 4 | Val-His-Thr-Pro-NH$_2$ | — |

It is clear from FIG. 5 that the ratio of β-isomerised and nonisomerized peptides (peptides 1 and 2) are closer, whereas in the case of peptide 3 the ratio of β-isomerised and nonisomerized peptides increased to 3:1 (FIG. 6). Then, it can be seen that peptide structure affects the relative ratios of isoaspartate formation from different sequences. It seems important to evaluate whether sequence difference around the different sites might provide an explanation for the different ratios of isoaspartate formation (19,20,21,22).

Biological Activity of Urinary Peptide Analogues

The action of the peptide analogues in the regulation of glycogen metabolism was examined. The experimental results (FIG. 7) on the insulin-stimulated glycogen synthesis in isolated rat muscle indicated that the biological activity of Val-His-Thr-Asp (SEQ ID NO:6) was much higher than that of any other peptide, and the nonisoaspartate peptides were more active than the isoaspartate peptides. When the residue Asp of the Val-His-Thr-Asp (SEQ ID NO:6) peptide was isomerised to Val-His-Thr-βAsp (SEQ ID NO:10), the biological activity of this isoaspartate peptide, at a peptide concentration of 0.1 mM, was reduced to 46%. The effects of Asp-His-Thr-Gly (SEQ ID NO:7) and βAsp-His-Thr-Gly (SEQ ID NO:11) on glycogen synthesis were also detected. However, no appreciable stimulation was detected with the peptide analogues Val-His-Thr-Pro (SEQ ID NO:8) in comparison with the control.

The in vivo effect on blood glucose level was observed after administration of the peptide (UP-401) at a dose of 3 mg/kg body weight. The maximal decrease in blood glucose level was found in the male Zucker fatty (fa/fa) rats 60 min after treatment with UP-401 (3 mg/kg). The degree of blood glucose reduction varied with different peptide analogues (Table 3). When the Val-His-Thr-Asp-NH$_2$ (UP-402) (SEQ ID NO:6) peptide was administered at a dose of 3 mg/kg body weight, the blood glucose level was reduced to a maximum of 0.95 mol/L. Increasing the dose of Val-His-Thr-Asp (SEQ ID NO:6) peptide to 4.5 mg/kg body weight, the effect was prolonged to 120 min (FIG. 8). Under the same conditions the Val-His-Thr-βAsp (SEQ ID NO:10) peptide was also tested for-its effect on blood glucose levels. No significant difference between Val-His-Thr-Asp (SEQ ID NO:6) and Val-His-Thr-βAsp (SEQ ID NO:10) on the blood glucose levels was observed.

TABLE 3

Reduction of blood glucose level (in vivo insulin-like effects of tetrapeptide on glucose metabolism).

| Time (min) | 402 (3 mg) | 402 (4.5 mg) | 401 (3 mg) | 404 (3 mg) | Control (Saline) |
|---|---|---|---|---|---|
| 15 | −0.26 | −0.43 | −0.50 | −0.21 | −0.1 |
| 30 | −0.62 | −1.03 | −0.91 | −0.54 | 0.2 |
| 45f | −1.21 | −1.50 | −1.1 | −0.77 | 0.1 |
| 60 | −1.25 | −1.45 | −0.93 | −0.95 | 0.1 |
| 75 | −0.64 | −1.52 | −0.64 | 0.23 | 0 |
| 90 | 0.05 | −1.35 | −0.08 | −0.03 | 0.1 |
| 120 | | 0.07 | | | |

Discussion

In this study, a series of synthetic peptide analogue of the UP-401 peptide, from UP-402 to UP-407, were designed, prepared and tested to investigate the structure-activity relationship (SAR)

Results suggested that a hydrophobic amino acid at the position 1 could significantly enhance the insulin-potentiating effect of the UP-401 peptide. In vitro data indicated that a 68% higher glycogen synthesis was found by the effect of UP-402, an analogue with the substitution of Gly by Val. On the other hand, replacement of Gly with the hydrophilic amino acid, Asp (UP-403) or isoAsp (UP-407), reduced the peptide activity.

Results also suggested that the position 4 of the UP-401 peptide was critical to biological activity of the UP-401. Analogues with replacement of on Asp by another amino acid like Gly (UP-403), or Pro (UP-404) or even isoAsp (UP-406) all reduced the potency of the parent UP-401. The biopotency of UP-402, a better analogue, was also reduced by the replacement of Asp by isoAsp, which further indicated that the Asp at the position 4 is essential for the biological activity. Thus, all the evidence strongly suggested that the $Asp^4$ residue plays an important role for the activity of UP-401, since changes by substitution and isomerisation reduced the potency of the molecule.

These investigations have also provided a better insight in the design and synthesis of structurally related Thr-Asp site active centre sequences. It has been found that the ratio of nonisoaspartate with isoaspartate in the sequence of Gly-His-Thr-Asp (SEQ ID NO:5) was very similar to that of sequence Val-His-Thr-Asp. Under the same condition a ratio of nonisoaspartate and isoaspartate is 1:3 (FIG. 6), it might be that the nitrogen atom of the side of histidine residue could help deprotonation of the nitrogen in peptide bond, by achieving the necessary nucleophilic character to form a succinimide product (22,23,24,25). On the other hand, the degree of steric hindrance by the side-chain of the N+1 residue is the crucial factor directly to effect the stability of the molecule (26) The nonisoaspartate peptide with Thr-Asp site exhibited higher hypoglycaemic action than that of the isoaspartate analogue as found during iv injection with overnight-fasted Zucker fatty (fa/fa) rats (FIG. 8).

Persons skilled in this art will appreciate that variations and modifications may be made to the invention as broadly described herein, other than those specifically described without departing from the spirit and scope of the invention. It is to be understood that this invention extends to include all such variations and modifications.

REFERENCES

1. Donahue R. P., Abbott R. D. Reed D. M., Katsuhiko Y., (1987) *Diabetes* 36, 689–692.
2. Fuller, H. H., Shipley, M. J., Rose, G., Jarrett, R. J., Keen, H., (1980) *Lancet* 1, 1373–1376.
3. Jarrett, R. J., McCartney, P. and Keen, H., (1982) *Diabetologia* 22, 79–84.
4. Report of the Expert Committee on the Diagnosis and Classification of Diabetes Mellitus.
    Diabetes Care 1997 July; 20(7): 1183–97.
5. Amos A F, McCarty D J, and Zimmet, (1994) Diabetic Medicine Volume 14 (Supplement 5).
6. Isaksson O. G. P, Schwartz J., Kostyo, J. L., and Reagan, C. R., (1978) *Endocrinology* 105:452–458.
7. Isaksson, O. G. P., Eden, S, and Jansson, J., (1985), Ann. Rev. Physiol. 47:483–499
8. Ng, F. M., (1993), *Expr. Clin. Endocrinol* (Life Sci. Adv.) 12:129–139
9. Lim, N., Ng, F. M., Wu, Z. M., Ede, N. and Hearn, M. T. W., (1992) *Endocrinology*, 131, 835–840.
10. Zimmet, P. Z., *PhD Thesis*, Monash University (1973)
11. Ng, F. M., Zimmet, P. Z., Swiler, G., Taft, P. and Bomstein, J. (1974) *Diabetes* 23, 950–56.
12. Wellings, D. A., and Atherton, E., (1997) In *Methods in Enzymology*, Vol. 289, pp 44–66
13. Merrifield, R. B., (1963) *J. Am. Chem. Soc.*, 85, 2149.
14. Barany, G., Kreib-Cordinia, N., and Mullen, D. G., (1988), In *Encyclopedia of Polymer Science & Engineering*, $2^{nd}$ Edition, Vol. 12. pp 811–858
15. Geiger, T. and Clarke, S., (1987) *J. Biol. Chem.* 262, 785–794.
16. Stephenson, R. C., and Clarke, S., (1989), *J. Biol Chem.*, 264 6164–6170
17. Van Handel E, (1965) *Anal Biochem.*, 11, 256–265.
18. Thompson, P. E., Lim, N., Ede, N. J., NG, F. M., Rae, I. D., & Hearn, M., (1995) *Drug Design & Discovery* 13:55–72
19. Murray, E. D., Jr. and Clarke, S. (1984) *J. Biol Chem.*, 259, 10722–10732.
20. Clarke, S. (1987) *Int. J. Pept. Protein Res.*, 30, 808–821.
21. Stephenson, R. C. and Clarke, S. (1989) *J. Biol. Chem.* 264, 6164–6170.
22. Bernhard, S. A., Berger, A., Carter, J. H., Katchalski, E., Sela, M. and Shalitn,Y. (1962) *J. Am. Chem. Soc.*, 84, 2421–2434.
23. Folsch, G. (1966) *Acta. Chem. Scand.*, 20, 459–473.
24. Piszkiewics, D., Landon, M., and Smith, E. L. (1970) *Biochem. Biophys. Res. Commun.*, 40, 1173–1178.
25. Brennan, T. V. and Clarke, S. (1993) *Protein Science*, 2, 331–338.
26. Fledelins, C., Johnson, A. H., Cloos, P. A. C., Bonde, M. and Qvist, P. 91997) *J. Biol Chem.*, 272, 9755–9763.

The invention claimed is:

1. An isolated peptide selected from:
Gly-His-Thr-Asp (SEQ ID NO:5); and Val-His-Thr-Asp (SEQ ID NO:6).

2. An isolated peptide according to claim 1, wherein the amino acids are in the L-form.

3. A method of regulating in vivo blood glucose levels in a human or other mammal, which comprises administration to said human or other mammal of an effective amount of an isolated peptide of the formula:

$(Xaa)_{n1}$-$Xaa_1$-His-Thr-Asp-$(Xaa)_2$ (SEQ ID NO:2)

wherein
Xaa is any amino acid;
$Xaa_1$ is a hydrophobic amino acid;
$n_1$ is 0–10; and
$n_2$ is 0–10.

4. A method according to claim 3, wherein the peptide is a peptide of the formula:
or

```
(Xaa)n1-Gly-His-Thr-Asp-(Xaa)n2 or    (SEQ ID NO: 3)

(Xaa)n1-Val-His-Thr-Asp-(Xaa)n2       (SEQ ID NO: 4)
``` wherein Xaa, $n_1$ and $n_2$ are as defined in claim 3.

5. A method according to claim 3, wherein the peptide is selected from:

```
Gly-His-Thr-Asp; and    (SEQ ID NO: 5)

Val-His-Thr-Asp.        (SEQ ID NO: 6)
```

6. A method according to claim 3, wherein the regulation of in vivo blood glucose levels is for treatment of diabetes in a human.

7. A pharmaceutical composition for regulating in vivo blood glucose levels in a human or other mammal, which comprises an isolated peptide of the formula:

$(Xaa)_{n1}$-Gly-His-Thr-Asp-$(Xaa)_{n2}$ (SEQ ID NO:3) or
$(Xaa)_{n1}$-Val-His-Thr-Asp-$(Xaa)_{n2}$ (SEQ ID NO:4)

wherein
Xaa is any amino acid;
$n_1$ is 0–10; and
$n_2$ is 0–10,
together with one or more pharmaceutically acceptable carriers and/or diluents.

8. A composition according to claim 7, wherein the peptide is selected from:

```
Gly-His-Thr-Asp; and    (SEQ ID NO: 5)

Val-His-Thr-Asp.        (SEQ ID NO: 6)
```

9. A method according to claim 6, wherein the regulation of in vivo blood glucose levels is for treatment of Type 2 diabetes in a human.

* * * * *

UNITED STATES PATENT AND TRADEMARK OFFICE
CERTIFICATE OF CORRECTION

PATENT NO. : 7,173,012 B2  
APPLICATION NO. : 10/481662  
DATED : February 6, 2007  
INVENTOR(S) : Paul Zev Zimmet et al.

It is certified that error appears in the above-identified patent and that said Letters Patent is hereby corrected as shown below:

Column 19  
Line 21, "$(Xaa)_{n1}$-$Xaa_1$-His-Thr-Asp-$(Xaa)_2$(SEQ ID NO:2)" should read as  
-- $(Xaa)_{n1}$-$Xaa_1$-His-Thr-Asp-$(Xaa)_{n2}$     (SEQ ID NO:2) --

Lines 29-38,  
"4. A method according to claim 3, wherein the peptide is a peptide of the formula:  
or  
$(Xaa)_{n1}$-Gly-His-Thr-Asp-$(Xaa)_{n2}$ or     (SEQ ID NO: 3)  
$(Xaa)_{n1}$-Val-His-Thr-Asp-$(Xaa)_{n2}$     (SEQ ID NO: 4)  
wherein Xaa, $n_1$ and $n_2$ are as defined in claim 3." should read as  
-- 4. A method according to claim 3, wherein the peptide is a peptide of the formula:  
$(Xaa)_{n1}$-Gly-His-Thr-Asp-$(Xaa)_{n2}$     (SEQ ID NO: 3)  
or  
$(Xaa)_{n1}$-Val-His-Thr-Asp-$(Xaa)_{n2}$     (SEQ ID NO: 4)  
wherein Xaa, $n_1$ and $n_2$ are as defined in claim 3. --

Signed and Sealed this

First Day of July, 2008

JON W. DUDAS  
*Director of the United States Patent and Trademark Office*